United States Patent [19]

Gemmell

[11] Patent Number: 4,502,164

[45] Date of Patent: Mar. 5, 1985

[54] DEVICE FOR DESTROYING BACTERIAL FLORA

[76] Inventor: Leslie W. Gemmell, 72 Silverdale Rd., Eaglemont, Victoria, Australia

[21] Appl. No.: 508,983

[22] Filed: Jun. 27, 1983

Related U.S. Application Data

[63] Continuation of Ser. No. 211,754, Dec. 1, 1980, abandoned.

[51] Int. Cl.³ .................. A61L 2/04; E03C 1/126
[52] U.S. Cl. .................................... 4/191; 4/222;
210/175; 219/306; 219/309; 219/326; 422/1;
422/105; 422/106; 422/116; 422/119
[58] Field of Search .............. 422/1, 105, 49, 106,
422/116, 243, 291, 38, 112, 114, 119; 4/191,
197, 222; 219/309, 306, 326; 210/774, 175

[56] References Cited

U.S. PATENT DOCUMENTS

| | | | |
|---|---|---|---|
| 1,595,819 | 8/1926 | Bluemlein | 219/309 |
| 1,718,865 | 6/1929 | Macy | 219/326 |
| 1,916,804 | 7/1933 | McNab | 422/49 |
| 2,452,367 | 10/1948 | Gangloff | 219/535 |
| 3,808,609 | 5/1974 | Andersson et al. | 210/175 |

FOREIGN PATENT DOCUMENTS

| | | | |
|---|---|---|---|
| 20157 | 12/1980 | European Pat. Off. | 422/1 |
| 1316098 | 5/1973 | United Kingdom | 219/535 |

*Primary Examiner*—Barry S. Richman
*Attorney, Agent, or Firm*—Mattern, Ware, Stoltz & Fressola

[57] ABSTRACT

A device for destroying bacteria which accumulates in drainage pipes and the like. Previously, no device has been provided which will destroy bacteria which accumulates in drainage pipes.

This invention provides a housing (5,58) provided in the S-bend of a drainage pipe and includes a heating element (32,34,68) which causes water and bacteria which gathers in the housing (5,58) to boil to destroy bacteria. Heat is also transferred to the drainage pipe to destroy any bacteria which gathers on the side of the pipe.

The invention may also include a timer (80) to supply power to the heating means (32,34,68) for a desired amount of time and also may include an automatic actuator (62) which causes the timer (80) to supply power to the heating means (32,34,68) when water and/or contaminated matter passes down the drainage pipe.

18 Claims, 7 Drawing Figures

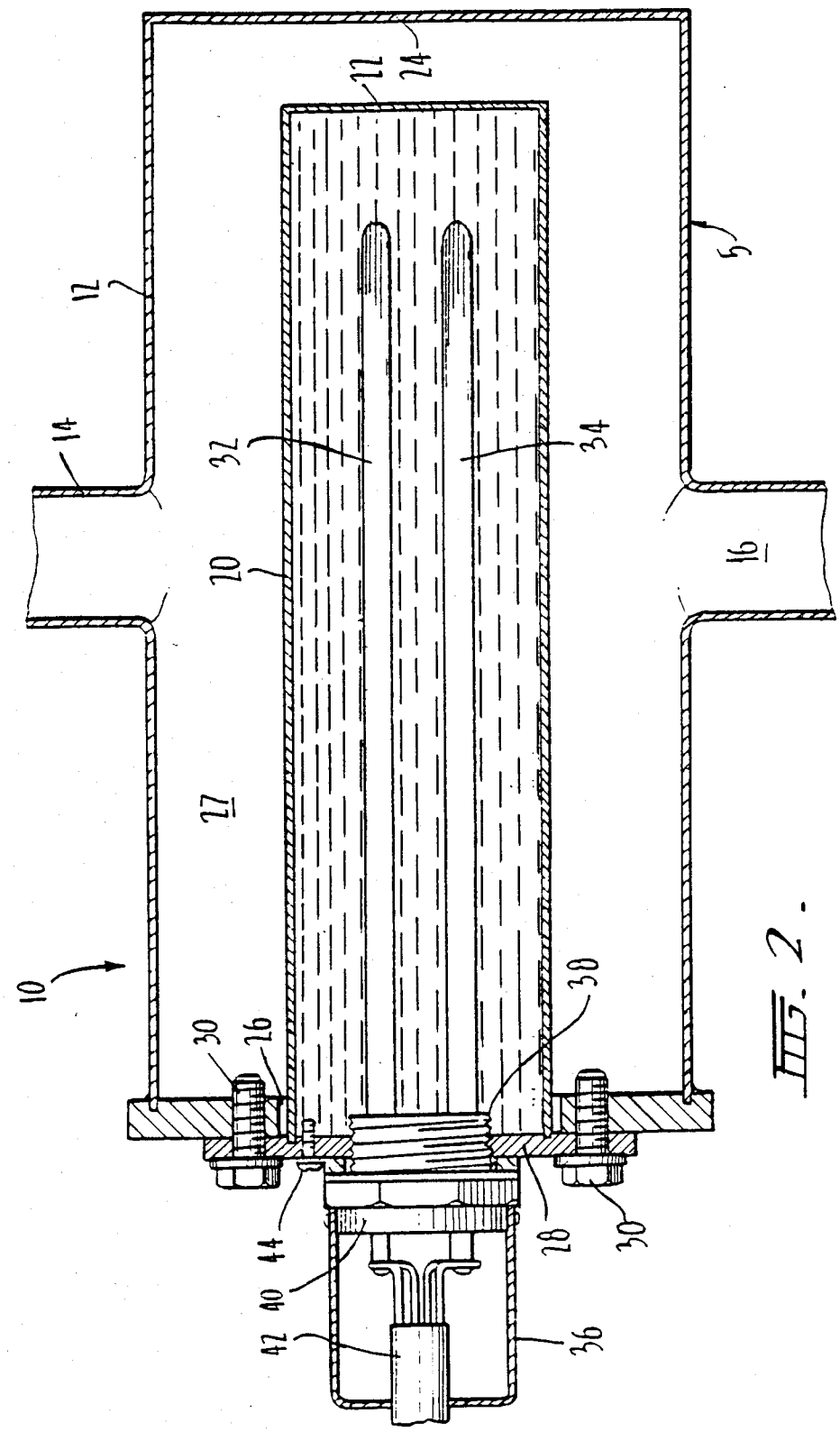

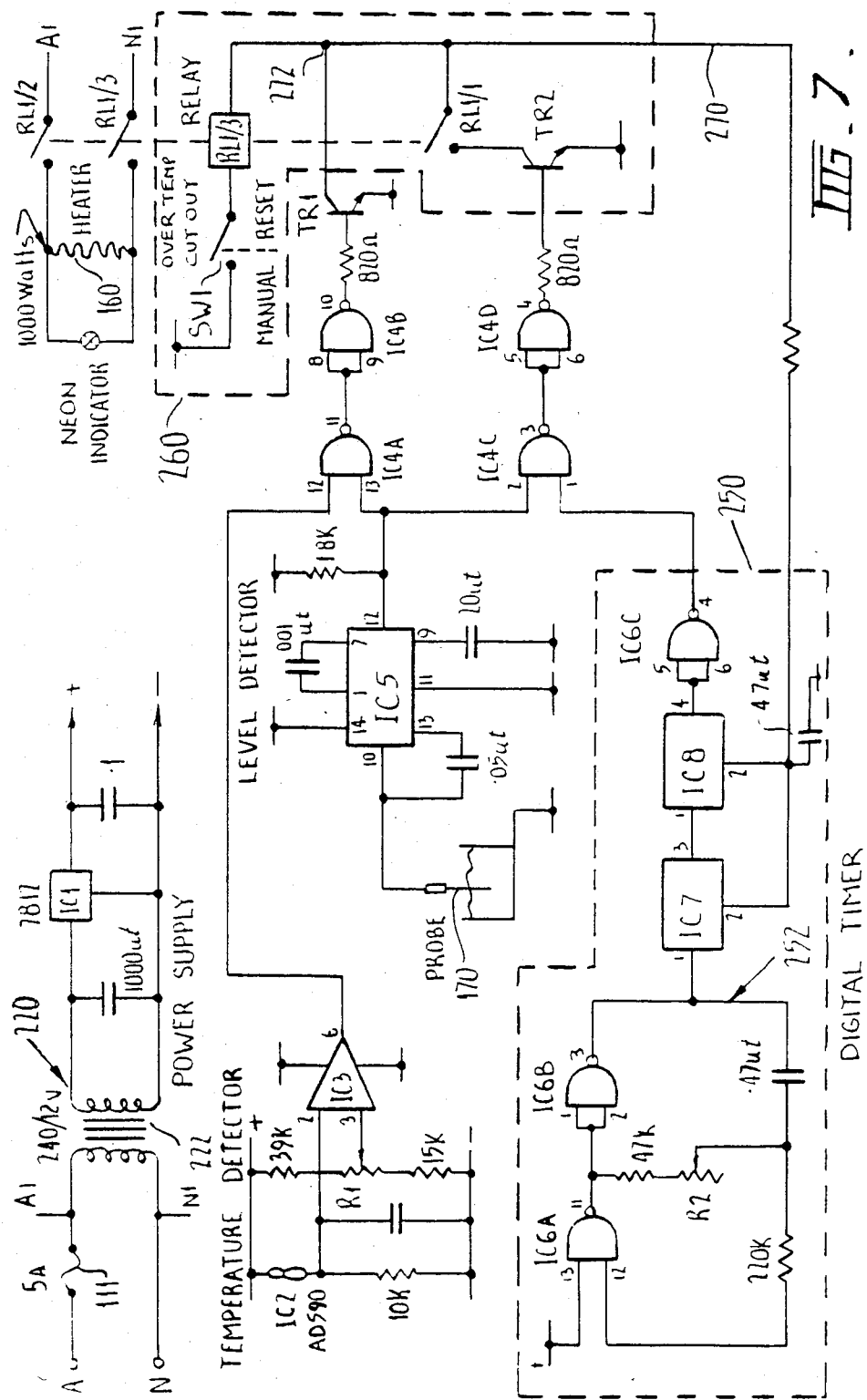

DEVICE FOR DESTROYING BACTERIAL FLORA

This application is a continuation of application Ser. No. 211,754, filed Dec. 1, 1980, and now abandoned.

This invention relates to a device for destroying bacterial flora by the sterilization of contaminated waste which contains the bacterial flora.

In hospitals, for example, waste materials are often disposed of by pouring the material down sinks and the like. This waste material may therefore gather in the S-bends or the like, of drainage pipes where bacterial flora in the waste material flourishes.

The bacterial flora which builds up on the drainage pipe is extremely dangerous, particularly in the hospital environment where it is possible that sterile equipment may be contaminated by the bacterial flora. Indeed, it has been known for a patient in a hospital to contract a sickness which has been attributed to bacterial flora contamination of instruments which have been used in connection with the patient. The present invention seeks to overcome this problem by providing a device which will destroy bacterial flora which gathers in the drainage pipes.

The present invention may therefore be said to reside in a device for destroying bacterial flora by sterilization of contaminated waste which contains the bacterial flora, said device comprising a housing, said housing has an inlet to allow waste material to pass into said housing, heating means in said housing for heating the waste material such that any bacterial flora which gathers in or on said housing may be sterilized by heat from said heating means, to thereby destroy said bacterial flora.

Preferably, the device of this invention is adapted to be placed in a drainage pipe between a sink and an outlet of the S-bend of the drainage pipe.

Accordingly, any bacterial flora which does not pass completely through a drainage pipe to which the device is connected and in fact collects on the drainage pipe, and in the housing will be destroyed by heat passing through the housing and by boiling water in the housing.

Most preferably, the heating means comprises a heating element and the housing comprises a cylinder located in the S-bend of the drainage pipe, the heating element extending longitudinally in the cylinder such that waste material flushed down the sink with water gathers in the cylinder whereby the water is boiled by the heating element and heat is conducted through the drainage pipe via steam and the boiling action of the water and waste material to destroy bacteria in the water as well as bacteria which collects on the inside of the drainage pipe. Preferably, the device includes an actuator which automatically actuates the heating element when water or the like passes down the drainage pipe.

In a second embodiment, said housing is defined by a first member which receives a second member therein, the first member being at least partially spaced from the second member.

Preferably, the second member is in contact with said first member along one side and said second member contains said heating means such that heat from the heating means may be conducted from the second member to the first member.

Preferably, the heating means comprises two heating elements releasably sealed within said second member, said second member containing fluid for conducting heat from the elements to the second member.

Preferably, the fluid is oil and preferably the housing has an outlet for allowing contaminated waste to pass from the housing.

A preferred embodiment of the invention will be described with reference to the drawings in which:

FIG. 2 is a longitudinal, cross-sectional view of the device of FIG. 1,

Figure 1:
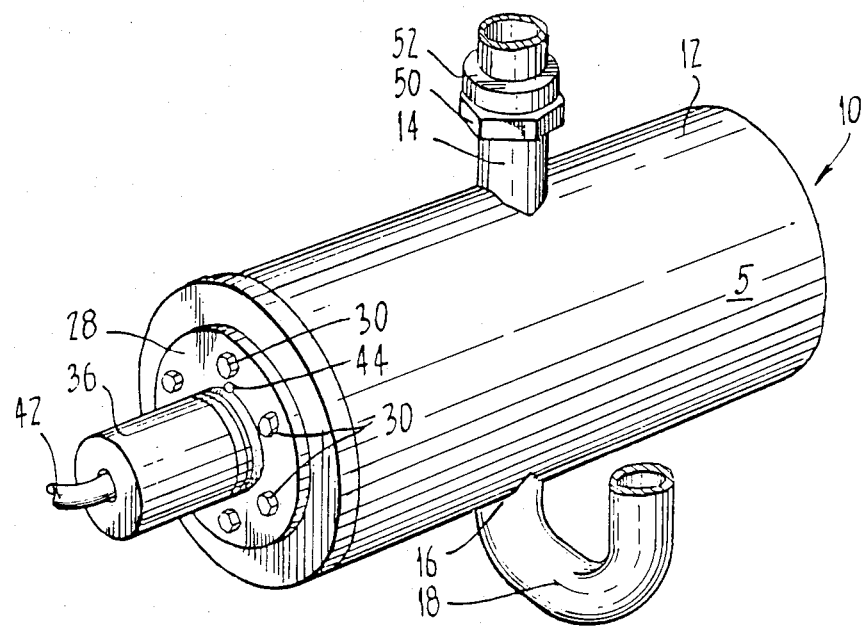
FIG. 1 is a perspective view of a device embodying the invention.

Referring to FIGS. 1 and 2, the device 10 comprises first outer member 12 of generally cylindrical form. The first member 12 has an inlet 14 and an outlet 16. The outlet 16 may be a straight pipe which is connected with a drainage pipe (not shown) above the S-bend thereof or it may have an S-bend 18 integral therewith.

A second cylindrical member 20 is provided in the first member 12 and forms a housing 5 as best seen in FIG. 2 and is spaced from the first member at their ends 22 and 24 and about the circumference of the members. The first and second members define a housing 27 in which contaminated waste can gather as will be explained hereinafter.

The outer member 12 has an open end 26 which is closed by a plate 28 rigidly connected to the second cylindrical member 20 when the second cylindrical member 20 is located within the first member 12.

The plate 28 is connected to the first member 12 by bolts 30 to securely maintain the second member 20 within the first member 12.

A pair of heating elements 32 and 34 are removably located in the second member 20. The elements 32 and 34 are held in a cap 36 which is screw threaded by thread 38 into an opening in the plate 28 which opening is provided with a cooperating screw thread. The elements 32 and 34 are supported by a support 40 and are independently powered by electrical energy supplied via an insulated conductor 42.

An air bleed 44 may be provided through plate 28 to allow escape of any air from the interior of the second member 20. The second member 20 is filled with a fluid having a high boiling point, for example, non-carbon oil.

Figure 3:
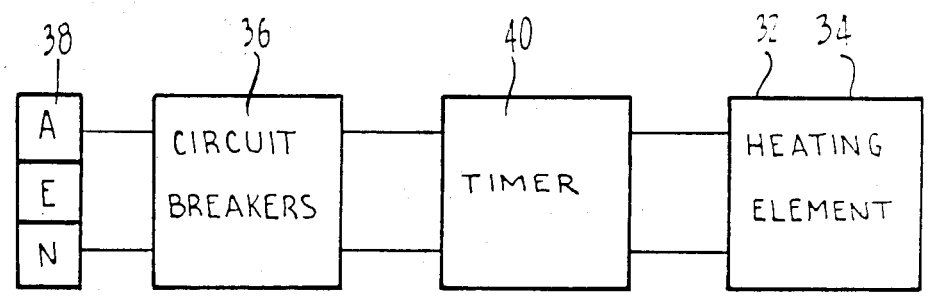
FIG. 3 is a schematic diagram of a circuit for supplying power to the device of FIGS. 1 and 2.

FIG. 3 shows a schematic circuit diagram for supplying power to the heating elements 32 and 34. The electrical energy is first conveyed through circuit breakers 36 from a conventional 240 V outlet 38 to a timer 40 and then to the elements 32 and 34. The circuit breaker is used to disconnect power in the event of a failure in the heating elements 32 and 34 which may otherwise cause a "black out" in the area in which the device is used. The circuit breakers 36 are particularly advantageous if the device is to be used in a hospital to prevent any possibility of power supply disruption to essential equipment maintained in the hospital.

The timer 40 which may be a Venner synchronous motor-driven multiset time switch may be used to selectively supply power to the elements 32 and 34 as it may not be necessary to continually heat the oil in the second member 20. Indeed, if the sink or the like, beneath which the device is connected is not used regularly, it may only be necessary to supply energy to the elements for a few hours a day.

In operation, contaminated waste which is poured into the sink will pass down the drainage pipe (not shown) and through the device 10. Generally, the contaminated waste will be flushed down the sink with water from a tap above the basin (not shown) to which the drainage pipe and device 10 are attached. As the waste passes through the device it will tend to build up on the inside surface of the first member 10 and on the outside surface of the second member 20 as well as in the S-bend 18. Electrical energy which is supplied to the elements 32 and 34 will cause the same to heat the oil contained with the second member 20. Since oil has a high boiling point, the oil will become extremely hot and conduct heat to the second member 20. The second member 20 will in turn conduct heat into the first member 12 with the result that the entire device 12 will become extremely hot. The heat will therefore destroy any bacterial flora which may be present in the waste which gathers in the device 10 and any water and waste trapped in the housing 5 will be boiled, which boiling will also destroy bacteria in this waste and the boiling water will assist in destroying bacteria on the inside of the drainage pipe. The extent of heat conduction in the inlet and outlet pipes 14 and 16 can be controlled by selecting an appropriate length of inlet and outlet pipe and securing the same to the drainage pipe with appropriate connections (for example, connectors 50 and 52 in FIG. 1) with a heat resistant gasket disposed therebetween.

Preferably, the first and second members 12 and 20 are fabricated from 16 gauge copper tube and the ends of these members which are joined are preferably silver braised.

Figure 4:
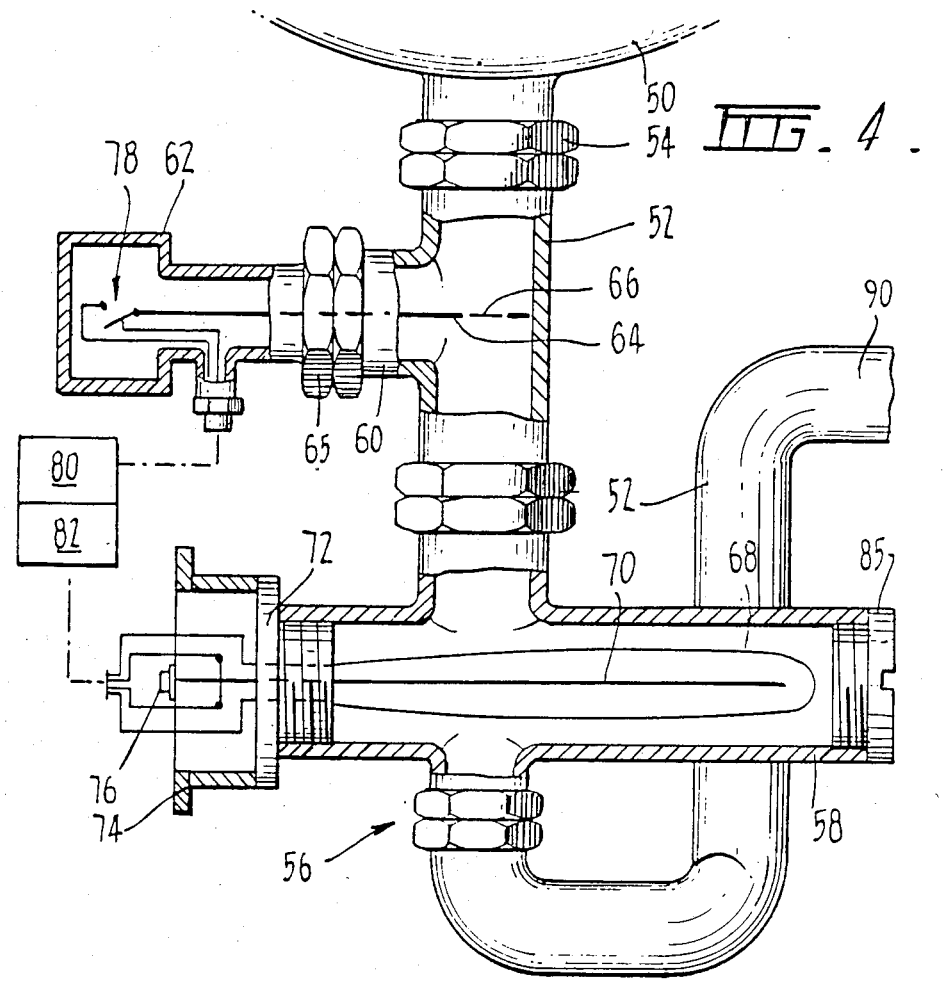
FIG. 4 is a sectional view of a second and preferred embodiment of the invention.
Figure 5:
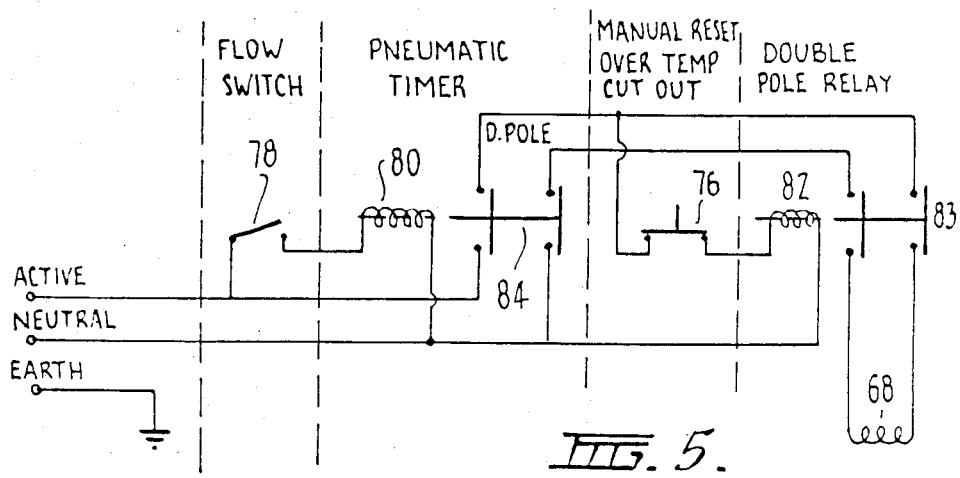
FIG. 5 is a circuit diagram for the embodiment of FIG. 4, FIGS. 6 and 7 are views and diagrams of a third embodiment.

In the second and preferred embodiment shown in FIGS. 4 and 5, a basin 50 has a drainage pipe 52 connected therewith by a coupling 54. Formed in the S-bend 56 of the pipe 52 is a water cylinder 58. The cylinder 58 may be formed integral with the pipe 52 or may be welded or otherwise coupled into the pipe. Above the cylinder 58, a branch 60 is provided and a flow switch 62, preferably a FS15 flow switch manufactured by M. E. Mack & Co. Pty. Ltd., of Box Hill, Victoria, Australia, is connected to the branch 60 by a coupling 65. The flow switch 62 includes a tongue or paddle 64 which extends into pipe 52 substantially across the diameter of the pipe 52. The tongue 64 has an aperture 66 therein to prevent waste material flushed down the sink from being trapped above the tongue 64.

The branch 60 and flow switch 62 form an angle α with the pipe 52 of preferably about 85° so that the branch is slightly inclined to prevent water from building up or remaining in the branch 60. The cylinder 58 includes a heating element 68 and a probe 70 of an over-temperature cut-out mechanism to be described hereinafter.

The heating element 68 and probe 70 are mounted on a member 72 which is screw-threaded into the cylinder 58 and contains contacts for supplying power to the element 68. A cover 74 is provided at the end of the cylinder 58 to house the member 72 and a manual reset cut-out switch 76.

The probe 70 has a bellows type heat sensor or thermostat, preferably that made by T. L. Thermatic Controls Ltd., Canada, certified under E53438 therein, which is coupled to the switch 76 so that when the temperature in the cylinder 58 reaches a predetermined value the bellows expands to open switch 76 which is normally closed.

The function of the flow switch 62 is well known and will therefore not be fully described. Suffice it to say that when the tongue 64 is contacted by water or waste material, the tongue is displaced downwardly in FIG. 4 to actuate a micro switch represented schematically at 78 to complete a circuit to a pneumatic timer 80. The timer 80 is preferably an Agastat (trade mark) 7000 Series timer made by Amerace Ltd of Ontario, Canada. The timer may be "pre-programmed" to supply power, once actuated for a predetermined amount of time, to the heating element 68 in combination with a double pole relay 82 preferably manufactured by N.H.P. Pty. Ltd., of Rivers Street, Richmond Victoria, Australia, the function of which shall be clear from the following description of FIG. 5.

Referring to FIG. 5 the micro-switch contact 78 which is normally open is closed by movement of tongue 64 when water or waste material is flushed down pipe 52. Closure of switch 78 supplies power to timer 80 which closes a double pole switch 84 which in turn supplies power to the double pole relay 82 which causes double pole switch 83 to close and thereby supply power to heating element 68.

The over temperature cut-out switch 76 is provided in the series circuit to the double pole relay 82 and is coupled to the bellows (not shown) located in probe 70.

If the temperature of the probe 70 reaches a predetermined value, for example a temperature indicative of the cylinder 58 boiling dry, the bellows (not shown) expands and causes switch 76 to open which in turn cuts off power to relay 82 which opens switch 83 to cut off power to element 68 to prevent the element from burning out. The switch 76 must be reset manually in order to again supply power to relay 82.

Since the cylinder 58 is located in S-bend 56 of the pipe 52, the cylinder will normally have water therein, which water forms the normal plug in the S-bend. Upon water and waste material being passed down pipe 52, the flow switch 62 will actuate the heating element 68 as detailed above, to cause the water and waste material in cylinder 58 and the remainder of the S-bend 56 to be heated.

As noted above, the timer 80 may be programmed to supply power for a predetermined amount of time. It has been found that about 6 minutes is required to boil the water in the S-bend 56 and depending upon the nature of the bacteria which accumulates in the pipe 52, an additional 2 to about 24 minutes may be required to destroy the bacteria in the pipe.

Accordingly, the timer 80 may be programmed to supply power to the element 68 for between 0 and 30 minutes to destroy bacteria, with about 8 to 10 minutes being found the most suitable time period. Once this period has elapsed the timer automatically shuts off power to the element and remains in this condition until actuated by the flow switch 62.

When actuated, the element 68 which is in contact with the water and waste material in the S-bend 56, boils the same to destroy bacteria therein. The boiling action in the cylinder causes boiling water to bubble throughout the pipe 52 and heat from the boiling water is circulated through the pipe 52, branch 60 and cylinder 58 to destroy any bacteria which may adhere to the surfaces of these members.

Any bacteria, which of course passes out of pipe 52 is not a problem since it is not capable of contaminating sterile equipment.

Heat resistant washers (not shown) may also be provided in the coupling 54 and at the outlet 90 of the pipe 52 to prevent heat conduction beyond pipe 52. A steam trap (not shown) may also be provided at the top of the pipe 52 to prevent steam from escaping from sink 50.

The cylinder 58 may have a screw threaded inspection plug 85 which may be unscrewed to allow the inside of the cylinder to be inspected.

The embodiments of this invention destroys substantially all bacteria which otherwise has been found to flourish in contaminated waste and the like which adheres to drainage pipes.

Figure 6:
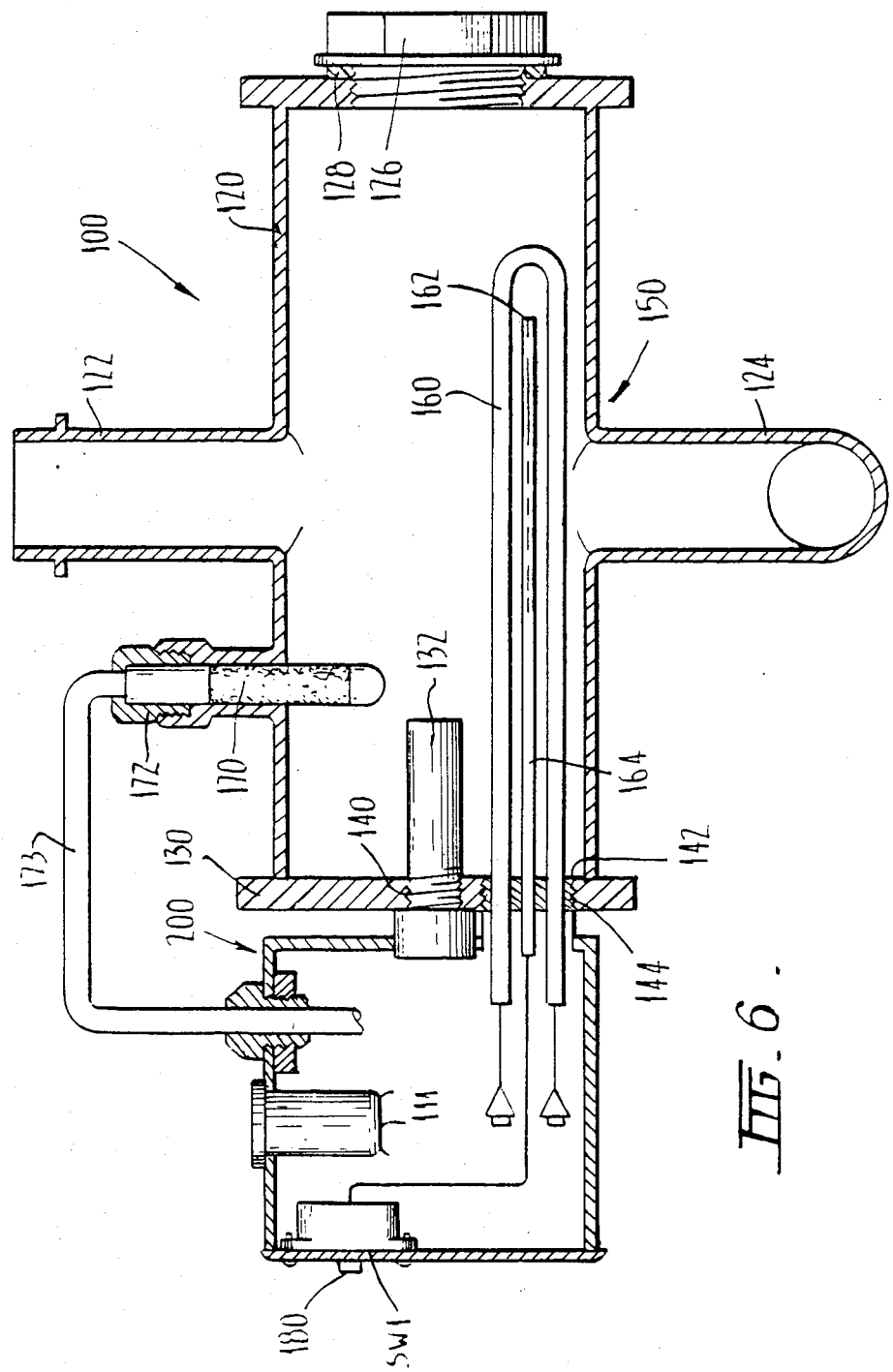

Referring first to FIG. 6 the device 100 embodying the invention is shown located in a water plug section 150 of a drainage pipe for example an S-bend. The device 100 includes a housing 120 having an inlet pipe 122 and an outlet pipe 124 both of which form part of the S-bend. The inlet and outlet pipes 122 and 124 are preferably provided with coupling flanges (not shown) and heat resistant gaskets which allow the pipes 122 and 124 to be connected to the remainder of the drainage pipe (not shown).

The housing 120 has one end provided with a removable plug 126 and a heat resistant gasket 128 which allows the interior of the housing to be inspected for purposes of maintenance and the like. The other end is permanently closed by a member 130 which has two openings, the purpose of which will be evident from the following. A first opening 140 receiving a closed sleeve 132 for housing an IC temperature sensor (not shown). The sleeve 132 is screwed into opening 140 by co-operating screw threads on the sleeve and opening. The second opening 142 receives a screw threaded plug 144 which carries a heating element 160 and a temperature sensor probe pocket 162 and the plug 144 is screwed into opening 142 to close that opening.

The pocket 162 carries a sensor probe 164 for measuring the temperature in the interior of the housing 120.

The probe 164 is preferably a bellows type heat sensor preferably made by TL.L. Thermatic Controls Ltd. Canada, No. 53438.

The housing 120 also has a liquid level detecting probe 170 projecting thereinto. The probe 170 is preferably a "low level probe" made and sold by L. W. Gemmell, 72 Silverside Road, Eaglemont Victoria 3084, Australia and the heating element 160 is made and sold by Stokes Australia Ltd., Sullon Street, Brunswick, Victoria, Australia.

The probe 170 is located in a housing 172 provided on the top of the housing 120 and the probe monitors the liquid level in the housing. If the liquid level falls below the level of the probe the operation of the unit will be stopped as will be described hereinbelow. Should the probe 170 fail, the probe 170, as will be described hereinbelow, also cuts off operation of the device and the device will not operate again until manual reset button 180 is depressed, to close manual reset switch SW1.

As can be seen from FIG. 6 a compartment 200 is located at one end of the housing 120 and the IC temperature sensor in sleeve 130, heating element 160 and probe 162 communicate with the compartment. Also the probe 170 communicates with the compartment 200 by cable 173. The compartment 200 housing the circuitory and timer etc. for operating the device which will be described with reference to FIG. 7.

As shown in FIG. 7 a conventional 240 V power supply 220 is stepped down to 12 V by a transformer 222. The stepped down 12 V supply is regulated by a voltage regulator, IC1 which is a 12 VDC voltage reguator No. 7812 made by Fairchild, and smoothed by filter capacitors as shown. The 12 V supply is converted to DC by a rectified diode (not shown) and is used to power the logic circuit to be described hereinafter. A 5 amp fuse 111 is provided in the 240 V power supply as shown.

The 240 V supply is also connected with heating element 160 through switches RL1/2 and RL1/3 to power the heating element 160. A neon indicator lamp 224 is provided in parallel with the heating element to indicate that power is being supplied to the heating element 160.

The heating element is controlled by the IC temperature sensor IC2 which is located in sleeve 130. The sensor IC2 is preferably a temperature sensor no. AD 590JH made by Analog Devices. The sensor IC2 produces a constant current output proportional to the temperature of the liquid in housing 120, which current is fed to ground via a resistor as shown to develop a voltage proportional to temperature. This voltage is compared with a preset voltage of 3.08 V across variable resistor R1 which is equal to a temperature of 35° C. An operation amplifier IC3 (no. 741C made by National Semiconductors) with open loop gain is used to compare the sensor and the voltage across resistor R1 and produce a high output when the temperature is below 35° C. The output of the operational amplifier is applied to one input of a two input NAND gate IC4A. The other input to NAND gate IC4A comes from probe 170 which will be described in detail hereinafter.

The output of gate IC4A is fed to a similar gate IC4B and then through a resistor to a switching transistor TR1. The swtiching transistor is connected to a relay which closes switches RL1/1, RL1/2 and RL1/3 when power is supplied to the relay. Accordingly if the sensor IC2 senses a temperature below 35° C. the output of the operational amplifier IC3 is high. The output from probe 170 is high if the water level in housing 120 is in the safe level condition i.e. above a certain level so that gate IC4A is supplied with two high inputs and therefore supplies a low input to gate IC4B which applies a high signal to transistor TR1 to turn the transistor on. This in turn powers relay RL1/3 to close switches RL1/1 to RL1/3 and power is supplied to heating element 160 to heat the water and waste material in housing 120. The switch RL1/1 ensures that relay RL1/3 remains latched to continue supply power to the heating element.

The probe 170 ensures that heating element 160 is not powered if the water level in housing 120 is below a predetermined level i.e. below the probe 170, wherein the heating element may burn out or be otherwise damaged due to lack of water in the housing 120.

If the liquid level is above a predetermined level i.e. above element 160 the output from the probe 170 and Fluid Detector IC5, which is preferably a Fluid Detector LM 1830 made by National Semiconductors is high thereby operating gate IC4A as described above. If the liquid level is lower than the predetermined level established by probe 170 the output from sensor IC5 is low and accordingly the output from gate IC4A is high the output from gate IC4B is low and transistor TR1 is not switched on. Therefore relay RL1/3 does not close switches RL1/1 to RL1/3 and power is not supplied to heating element 160. Power will not be supplied to heating element 160 until the liquid level is above the probe 170 and the temperature sensor IC2 senses a temperature below 35° C.

The probe 170 and temperature sensor IC5 will also stop supplying power to the heating element 160 if during a heating cycle the liquid drops below probe 170, which may occur if many heating cycles have occurred and no water has passed into the housing 120. The output of sensor IC5 is applied to a input of a two input NAND gate IC4C. The other input to IC4C is from digital timer 250 which will be described hereinafter. During a heating cycle input to gate IC4C from timer 250 will be high. Accordingly gate IC4C will apply a low output to gate IC4D which will ayply a high signal to transistor TR2 to turn the transistor on. It will therefore be seen that relay RL1/3 is powered by the circuit label 260.

If the liquid level is housing 120 drops below the level of probe 170 the output from sensor IC5 will go low therefore causing the gate IC4C to go high and the output of gate IC4D to go low thereby turning off transistor TR2 and disrupting power supply to relay RL1/3 to open switches RL1/1 to RL1/3 to cut off power to heating element 160.

The NAND gages IC4A to C are preferably made by National Semiconductor under No. 4011C.

The time the heating element 160 is powered to heat the liquid in the housing 120 is desirably about 17 minutes. This time is controlled by digital timer 250 which comprises an oscillator 250 which includes NAND gates IC6A and IC6B and which is continually in operation, counter IC7 and IC8 and NAND IC6C. The period of oscillation of the oscillator 252 is set by variable resistor R2 and applies a pulse to counter IC7 once every two seconds.

The counter IC7 is a seven stage counter and supplies a pulse from pin 3 to IC8 for every 128 pulses received from the oscillator 252. The counter IC8 is the same as the counter IC7 but applies a pulse from its pin 4 for every 32 pulses received. The output from counter IC8 is applied to gate IC6C which applies a lower output to NAND gate IC4C after every 4,096 oscillations of oscillator 252. Accordingly a high output is applied to gate IC4D and a low output is applied to transistor TR2 to turn the transistor off thereby disrupting power supply to relay RL1/3 to cut off power supply to the heating element 160.

The counters IC7 and IC8 are reset and commence counting on receiving of signals on line 270. When no power is supplied to relay RL1/3 due to transistor TR2 being in the off state point 272 experiences a high voltage which when applied to pin 2 of the counters IC7 and IC8 prevents the counters from counting. When the relay is powered to in turn close switches RL1/1 to RL1/3 the point 272 experiences low voltage which is applied to pin 2 of counters IC7 and IC8 and this results in the counters resetting to zero and allows the counters to commence counting, until the counter IC8 applies its high signal gate IC6C which as noted above cuts off the power to heating element 160 to end a heating cycle. The counters IC7 and IC8 are seven stage counters No. 4024 made by Texas Instruments and the gates IC6A to IC6C are Quad 2 input NAND gates No. 4011C made by National Semiconductors.

Further still a over temperature cut out switch SW1 is provided which is connected to bellows type probe 164. If the temperature in housing 120 reaches 120° C. the probe 164 expands and opens the switch SW1 to deactivate relay RL1/3 and cut off power to the heating element 160. The switch SW1 must be manually closed to allow the relay to be reactivated. Accordingly if for some reason the probe 170 etc should fail and not cut off power to the heating element 160 the probe 164 will sense that the heating element 160 is over heating and disrupt power to the heating element.

Accordingly the device will automatically heat the contents of the housing 120 for a period of 17 minutes and will automatically shut off power to the heating element after that time has elapsed and again activate the heating element if the temperature in the housing drops below 35° C. Also if the liquid level drops below a certain level or the temperature in the housing rises above a certain level power to the heating element will be disrupted thereby prevent damage to the heating element 160 or to the device itself.

When actuated the heating element 160 which is in contact with water and waste material in the S bend of a drainage pipe in which the device accordingly to the present embodiment is located, boils the water and waste material which forms the water plug in the S bend and which is located in the housing 160 to destroy bacteria therein. The boiling action in the cylinder causes boiling water to bubble through the S bend 150 and heat from the boiling water is circulated throughout the inlet and outlet pipe to the S bend to destory any bacteria which may adhere to the surfaces of these members. Any bacteria which of course passes out of the S bend is not a problem since it is not capable of contaminating sterile equipment.

Heat resistant washers (not shown) may also be provided for coupling the device 100 in a pipe to prevent heat conduction beyond the heat resistant washers. Steam trap (not shown) may also be provided at the top of the pipe between a sink or the like and the device 100 to prevent steam from escaping from the pipe.

It should also be noted that the integrated circuits shown in FIG. 7 will have power supplied to them from the 12 V supply and have their other pins connected in accordance with the details shown in FIG. 7 and the manufacturers specification.

Since modifications within the spirit and scope of the invention may readily be effected by persons skilled within the art, it is to be understood that this application is not limited to the particular embodiment described by way of example hereinabove.

The claims defining the invention are as follows:

1. A device for destroying bacterial flora by sterilization of contaminated waste which contains the bacterial flora within a drainage pipe associated with a waste trap, said device comprising a housing, said housing has an inlet to allow waste material to pass from said drainage pipe into said housing, heating means in said housing for heating the waste material such that any bacterial flora which gathers in or on said housing may be sterilized by heat from said heating means, a liquid temperature sensor for sensing the temperature of liquid within the housing, a housing temperature sensor for sensing the temperature of the housing, a probe mounted in the housing for sensing the level of liquid within the housing so as to change states if the level falls below a predetermined level, and temperature controlling means electrically connected to the liquid temperature sensor, the housing temperature sensor, the probe and the heating means, said temperature controlling means energizing the heating means for a predetermined time period if the sensed liquid temperature is below a first predetermined temperature value and if the liquid level is above its predetermined level; provided that, the housing temperature remains less than a second predetermined temperature value and the liquid level remains above its predetermined level; whereby the device safely destroys bacterial flora associated with contaminated device.

2. A device according to claim 1, wherein the housing includes means for inspecting the interior of the housing and further wherein the heating means comprises a heating element and the housing comprises a cylinder located in a water plug of the drainable pipe, the heating element extending longitudinally in the cylinder such that waste material flushed down the sink with water gathers in the cylinder whereby the water is boiled by the heating element and heat is conducted through the drainable pipe via steam and the boiling action of the water and waste material to destroy bacteria in the water as well as bacteria which collects on the inside of the drainage pipe.

3. A device according to claim 1 or 2 wherein the temperature controlling means includes a relay which is actuated when the temperature sensed by the liquid temperature sensor is below the first predetermined temperature value and when the liquid level sensed by the probe is above the predetermined level, said relay, when actuated, allowing the heating means to be energized.

4. A device according to claim 3 where the outputs from the probe and the liquid temperature sensor are applied to gate means which turns on a switching transistor when the liquid level is above the predetermined level and the temperature is below the first predetermined temperature value, said switching transistor, when switched on, causes the relay to be energized and thereby activates the heating means.

5. A device according to claim 1 or 2, further comprising a timer means to de-energize the heating means after the heating means has been energized for the predetermined time period.

6. A device according to claim 5, wherein said timer means comprises counter means which are provided with a signal of the commencement of operation of the heating means to set the counter means counting; a second gate means, the said counter means applying an output to the second gate means after a predetermined number of counts indicative of the predetermined time interval; a switching transistor connected to the second gate means and a relay controlled by the switching transistor so that upon an output generated by the counter means the switching transistor de-activates the relay so as to de-energize said heating means.

7. A device according to claim 1 or 2 wherein said device includes a manual reset switch intereconnected to the housing temperature sensor for preventing the heating means from being re-activated after it has been de-energized as a result of the housing temperature exceeding the second predetermined value until said switch is manually reset.

8. A device according to claim 1, wherein the housing temperature sensor includes a bellows and a switch such that when the bellows expands, it opens the switch to de-energize said heating means when the temperature exceeds the second predetermined temperature value.

9. A waste trap device for destroying bacterial flora by sterilization of contaminated liquid waste which contains the bacterial flora, said device comprising an elongate housing including means for connection to a drainage pipe, the longitudinal axis of the housing being transverse to that of the drainage pipe so as to form at least part of the water plug and thereby facilitate connection and maintenance of the device, heating means in said housing for heating the waste material such that any bacterial flora which gathers in or on said housing may be sterilized by heat from said heating means, means for controlling the heating means so as to maintain the temperature in the liquid waste above a predetermined value, said temperature controlling means further comprising means for sensing the temperature in the housing, said temperature sensing means being located in a lower portion of said housing, and a low level probe mounted through an upper portion of the housing so as to project into said housing, the probe interfaced with said heating means for sensing when liquid in the housing drops below a predetermined level and for causing the heating means to be de-energized when the liquid level drops below this predetermined level, the means for controlling the heating means responsive to the housing temperature sensing means for de-energizing the heating means when the housing exceeds a second predetermined temperature value, whereby the device safely destroys bacterial flora associated with contaminated waste.

10. A waste trap device as defined in claim 9 further comprising a manually operable switch interconnected with the housing temperature sensing means and the means for controlling the heating means so as to require the manual resetting of the switch if the housing temperature exceeds the second predetermined temperature value.

11. A waste trap device as defined in claims 9 or 10 wherein the housing further comprises an inspection opening at one of its ends so as to facilitate maintenance and inspection of the device.

12. A waste trap device as defined in claim 11 wherein the elongate housing comprises a cylinder for location in a water plug of the drainage pipe wherein the heating means comprises a heating element extending longitudinally in the cylinder such that liquid waste flushed down a sink associated with the drainage pipe gathers in the cylinder and is boiled by the heating element with the heat conducted through the drainage pipe via steam and the boiling action of the liquid waste so as to destroy bacteria in the liquid waste as well as bacteria which collects on the inside of the drainage pipe.

13. A waste trap device as defined in claim 12 wherein the means for controlling the heating means includes a liquid temperature sensor for sensing the temperature of the liquid within the housing.

14. A waste trap device as defined in claim 13 wherein the means for controlling the heating means includes a relay which is actuated when the temperature sensed by the liquid temperature sensor is below a first predetermined value and when the liquid level sensed by the low level probe is above the predetermined level; said relay, when actuated, allowing the heating means to be energized.

15. A waste trap device as defined in claim 14 wherein the means for controlling the heating means includes gate means and a switching transistor, the gate means interconnected with the outputs from the low level probe and the liquid temperature sensor so as to turn on the switching transistor when the liquid level is above the predetermined level and the temperature is below the first predetermined temperature value, the switching transistor when switched on causing the relay to be energized thereby activating the heating means.

16. A waste trap device as defined in claim 15 further comprising timer means to de-energize the heating means after the heating means has been energized for a predetermined time period.

17. A waste trap device as defined in claim 16 wherein the timing means comprises counter means that are provided with a signal at the commencement of operation of the heating means to set the counter means counting, a second gate means, the counter means applying an output to the second gate means after a predetermined number of counts indicative of the predetermined time period; a second switching transistor connected to the second gate means and a relay controlled by the second switching transistor so that upon an output generated by the counting means the second switching transistor deactivates the relay so as to de-energize the heating means.

18. A waste trap device as defined in claim 17 wherein the housing temperature sensor includes a bellows and a switch such that when the bellows expand, it opens the switch to de-energize the heating means when the temperature exceeds the second predetermined temperature value.

* * * * *